(12) United States Patent
Pianca

(10) Patent No.: US 6,389,320 B1
(45) Date of Patent: May 14, 2002

(54) IMPLANTABLE STIMULATION LEAD ADAPTABLE FOR STYLET OR GUIDEWIRE PLACEMENT

(75) Inventor: Anne M. Pianca, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/411,749

(22) Filed: Oct. 1, 1999

(51) Int. Cl.[7] .................................................. A61N 1/05
(52) U.S. Cl. ...................................... 607/122; 607/119
(58) Field of Search ................................. 607/119, 122, 607/125; 600/373, 374, 585

(56) References Cited

U.S. PATENT DOCUMENTS

| | | | | |
|---|---|---|---|---|
| 4,502,492 A | | 3/1985 | Bornzin | 128/785 |
| 5,330,520 A | * | 7/1994 | Maddison et al. | 607/122 |
| 5,398,683 A | * | 3/1995 | Edwards et al. | 607/122 |
| 5,803,928 A | * | 9/1998 | Tockman et al. | 607/122 |
| 5,851,227 A | * | 12/1998 | Spehr | 607/126 |
| 6,192,280 B1 | * | 2/2001 | Sommer et al. | 607/122 |

* cited by examiner

Primary Examiner—Carl Layno

(57) ABSTRACT

An implantable stimulation lead is readily adaptable for stylet placement or guidewire lead placement. The implantable lead includes at its distal end an implanting guide structure which includes a rigid member having a through bore. A plug is dimensioned to be received within the through bore and a retaining mechanism releasably retains the plug within the through bore. When the plug is retained within the through bore, the lead is adapted for stylet placement and when the plug is released from the through bore, the lead is adapted for guidewire lead placement. In a preferred embodiment, the distal electrode of the lead provides the rigid member of the implanting guide structure. After the lead is positioned by guidewire lead placement, the proximal end of the lead may be sealed with a plug or the plug of the implanting guide structure or new plug may be replaced or placed in the lead to prevent blood flow through the lead.

15 Claims, 5 Drawing Sheets

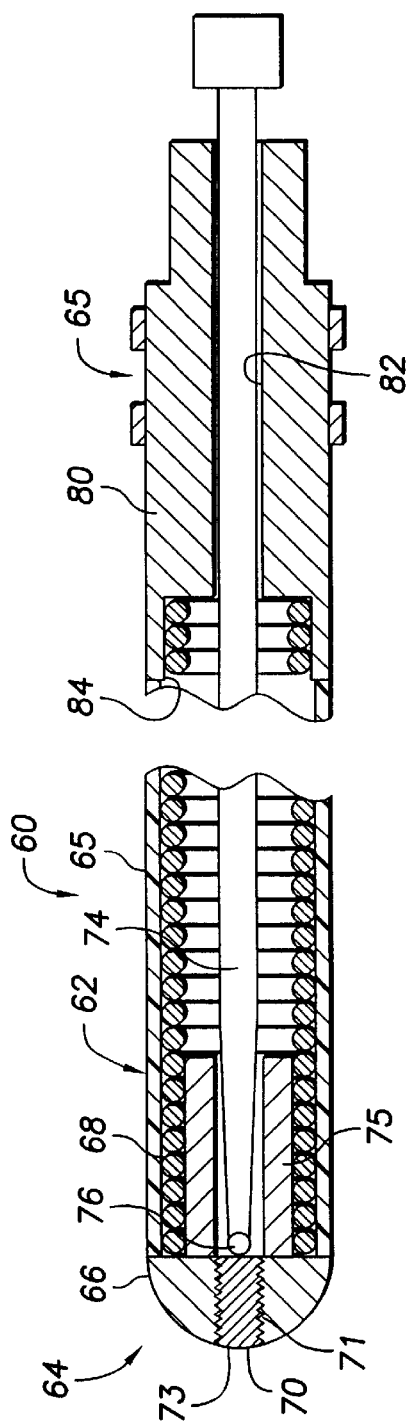
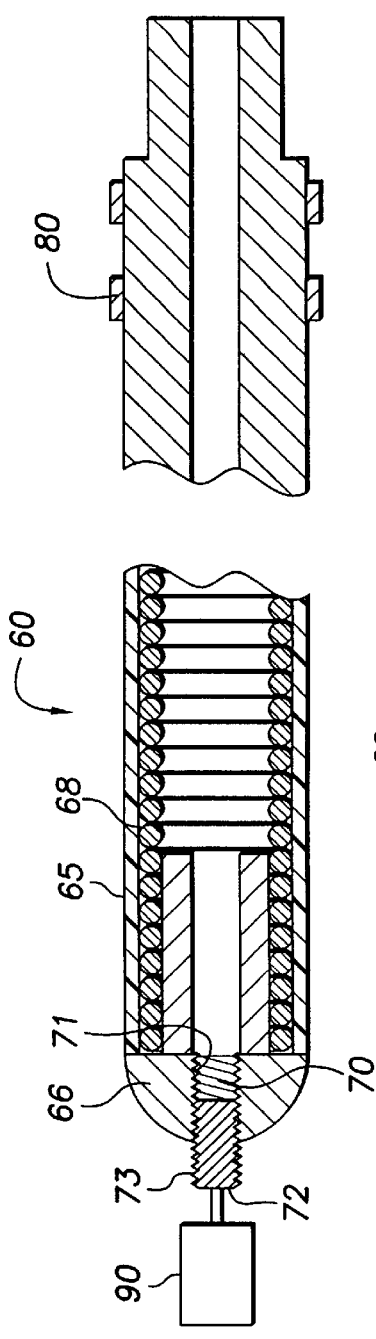
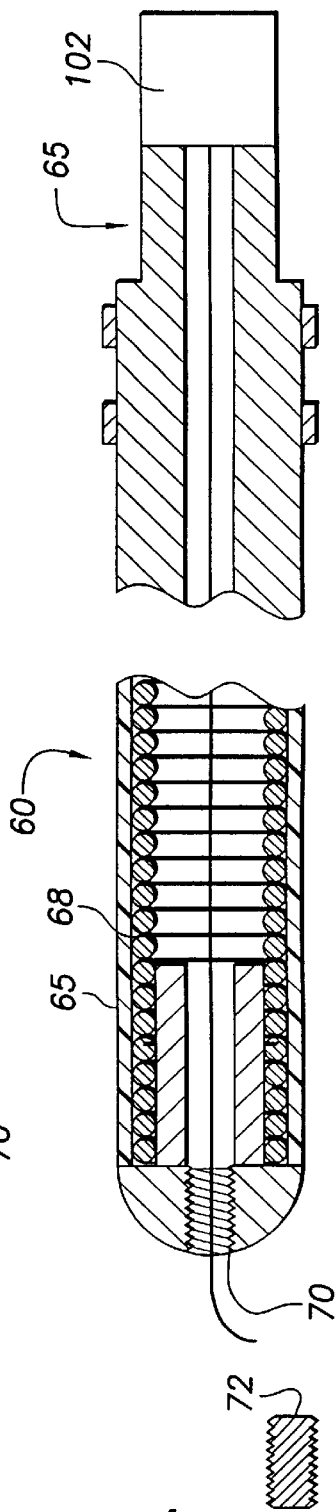
FIG. 4
FIG. 5
FIG. 6

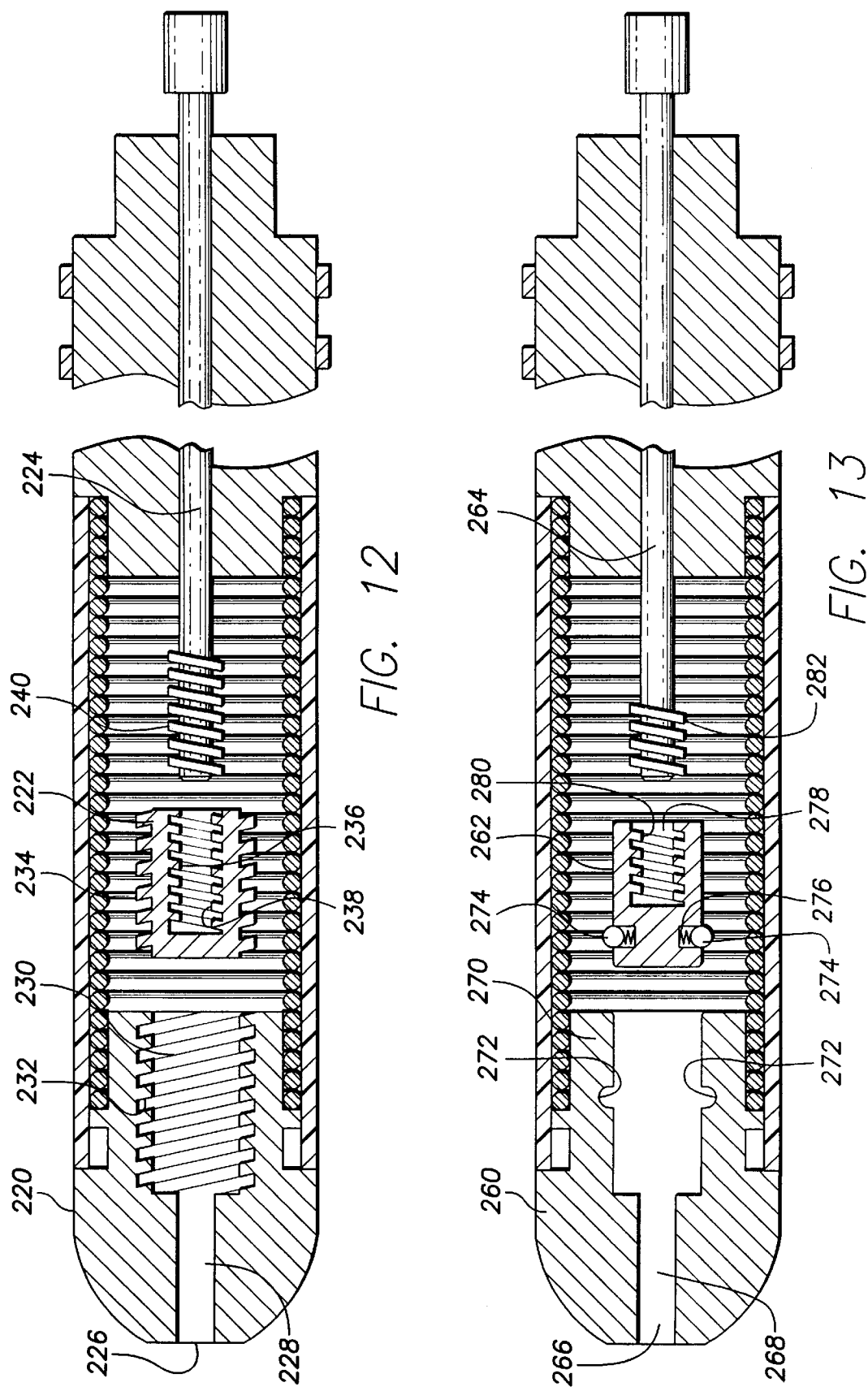

IMPLANTABLE STIMULATION LEAD ADAPTABLE FOR STYLET OR GUIDEWIRE PLACEMENT

FIELD OF THE INVENTION

The present invention generally relates to implantable cardiac stimulation leads for use with implantable cardiac stimulation devices. The present invention more particularly relates to a cardiac stimulation lead which is adaptable for either stylet placement or guidewire placement.

BACKGROUND OF THE INVENTION

Implantable cardiac stimulation devices are well known in the art. Such devices may include, for example, implantable pacemakers or defibrillators. The devices are generally implanted in an upper portion of the chest beneath the skin of a patient within what is known as a subcutaneous pocket.

Traditionally, therapy delivery has been limited to the right side of the heart. To that end, one or more stimulation leads are implanted within the heart. The leads may include one or more electrodes positioned within the right ventricle or right atrium, or both, of the heart for making electrical contact with their respective heart chambers. Conductors within the leads couple the electrodes to the device to enable the device to deliver the desired cardiac stimulation therapy.

Recently, cardiac stimulation leads and methods have been proposed and even practiced for delivering cardiac stimulation therapy from or to the left side of the heart. These lead structures and methods involve lead implantation within the coronary sinus and/or the great vein of the heart and/or coronary sinus veins, for example, since the coronary sinus is closely adjacent the left atrium and extends into the great vein which is adjacent the left ventricle of the heart. Electrodes thus placed in the coronary sinus and great vein may be used for various forms of cardiac stimulation therapy such as left atrial pacing, left ventricular pacing, and even cardioversion and defibrillation, for example.

Cardiac stimulation lead placement within the left side of the heart can require lead placement in difficult to reach veins and arteries. Two methods generally practiced for lead placement are stylet placement and guidewire placement. Stylet placement is a common practice for lead placement in the right side of the heart. Guidewire placement is less commonly employed.

Currently, there is debate in the art as to which lead placement method is best for lead placement in the left side of the heart. Each has its advantages and disadvantages. Stylet placement has the advantage of simplicity and involves minimal components, a sometimes important factor during a surgical procedure. In some patients with small veins or unusual cardiac vein anatomy, the guidewire placement method may have an advantage in facilitating lead placement. It is likely that both methods will find future use.

Cardiac stimulation leads are designed for only a specific lead placement methodology. More specifically, such leads are configured for either stylet placement or guidewire placement, but not both. Unfortunately, this may result in a physician finding, during an implant procedure, that a lead already attempted to be implanted must be discarded in favor of a lead designed for a different implanting method. This not only represents additional cost, but it also can complicate the surgical procedure.

The present invention provides an elegant solution to the aforementioned problem. More specifically, the present invention provides an implantable stimulation lead which is adapted for either stylet placement or guidewire placement. Not only is the lead so adaptable, the adaptation may be made easily, requires minimal components and may be accomplished with a tool already made available to the physician.

SUMMARY OF THE INVENTION

The present invention provides an implantable cardiac stimulation lead adaptable for either stylet placement or guidewire placement. The implantable cardiac stimulation lead includes an elongated body having a distal end and a proximal end. The lead further includes at least one electrode carried by the lead body, a connector at the proximal end of the lead body, and a conductor connecting the at least one electrode to the connector. The implantable cardiac stimulation lead further includes an implanting guide structure at the distal end of the lead body. The guide structure includes a rigid member including a through bore, a plug dimensioned to be received within the through bore, and a retaining mechanism that releasably retains the plug within the through bore. When the plug is retained within the through bore, the plug is arranged to engage a stylet for stylet placement of the lead. When the plug is released from the through bore, the through bore is arranged to receive a guidewire for guidewire placement of the lead.

In accordance with a preferred embodiment of the present invention, the implanting guide structure is formed by an electrode at the distal end of the lead body. The electrode includes the through bore, the plug configured to be received within the through bore, and the retaining mechanism that releasably retains the plug within the through bore.

The retaining mechanism may include complimentary threads carried by the plug and the through bore. In addition, the conductor which connects the electrode to the connector may include a stylet coil which guides the stylet to engage the plug for stylet placement and for guiding the guidewire from the through bore to the connector for guidewire placement.

In accordance with further aspects of the present invention, the plug is arranged for receiving a tool that may be used for retaining the plug within or releasing the plug from the through bore. The connector may include a retaining element for securing the connector to an implantable cardiac stimulation device and wherein the same tool which may be used for retaining the plug within and releasing the plug from the through bore may also be used in cooperation with the retaining element for securing the connector to the implantable cardiac stimulation device.

In accordance with still further aspects of the present invention, the connector includes a through bore and a second plug is dimensioned to be received within the connector through bore and releasably retained therein by a second retaining mechanism. The second plug serves to prevent blood flow into the connector top after the lead has been positioned by guidewire placement. Alternatively, for preventing blood flow into the lead, the implanting guide structure may be arranged to receive its plug at the proximal end of its through bore. This permits the plug to be replaced in the through bore from the proximal end of the lead following a guidewire placement.

BRIEF DESCRIPTION OF THE DRAWINGS

The above and other aspects, features, and advantages of the present invention will be more apparent from the following more particular description thereof, presented in conjunction with the following drawings wherein:

FIG. 4 is an exploded cross-sectional view illustrating a second implantable cardiac stimulation lead embodying the present invention adapted for stylet placement;

FIG. 5 is an exploded cross-sectional view of the lead of FIG. 4 illustrating the adaptation of the lead from a stylet placement configuration to a guidewire placement configuration;

FIG. 6 shows the lead of FIG. 4 adapted for guidewire placement;

FIG. 12 is an exploded, cross-sectional side view of an electrode, a plug, and a stylet tool to illustrate the manner in which the plug may be replaced in the electrode following guidewire placement; and FIG. 13 is an exploded, cross-sectional view of another electrode, plug, and stylet tool embodying the present invention.

DETAILED DESCRIPTION OF THE PREFERRED EMBODIMENTS

Figure 1:
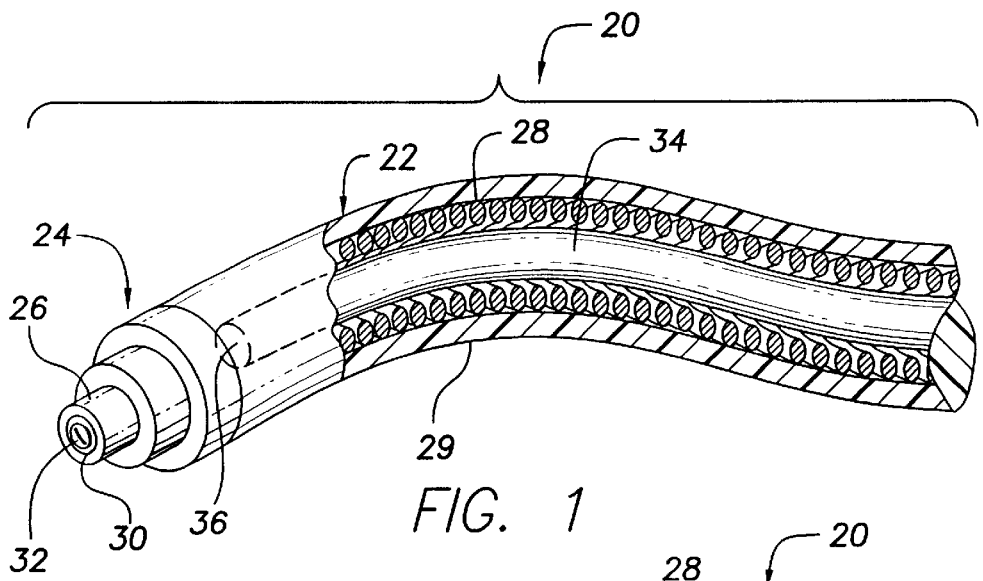
FIG. 1 is a partial perspective view and partial cross-section illustrating a first implantable cardiac stimulation lead embodying the present invention configured for stylet placement.

Referring now to FIG. 1, it illustrates an implantable cardiac stimulation lead 20 embodying the present invention. The lead 20 illustrated in FIG. 1 is particularly adapted for use with an implantable pacemaker. However, as those skilled in the art will appreciate from the description of the various embodiments to follow, any one of the embodiments of the present invention may be utilized with any implantable cardiac stimulation device which requires lead placement in a heart chamber or a vein of a patient.

The lead 20 includes an elongated lead body 22 having a distal end 24 and a proximal end (not shown). The lead 20 further includes an electrode 26 at the distal end 24 and a connector (not shown) at the proximal end. A conductor in the form of a coil 28, of the type well known in the art, connects the electrode 26 to the connector.

The lead 20 still further includes an outer insulation 29 of the type well known in the art. For example, the outer insulation may be formed from silicone rubber, polyurethane, or other material known in the art. The stylet coil may be formed of MP35N stainless steel alloy, platinum/iridium alloy, titanium, or other material known in the art. The electrode 26 and the plug 32 are preferably formed of a platinum iridium alloy or titanium as is known in the art.

In accordance with the present invention, the lead 20 may be utilized for stylet placement or guidewire placement. The lead 20 illustrated in FIG. 1 is configured for stylet placement. To that end, the electrode 26 forms an implanting guide structure at the distal end 24 of the lead 20. The electrode 26 includes a through bore 30 and a plug 32 dimensioned to be received within the through bore 30. As may be seen in FIG. 1, the plug 32 is retained within the through bore 30. Within the lead is a stylet 34. The stylet 34 has a distal end 36, which is arranged to engage the electrode. 26 for guiding the lead 20 to a desired position within a heart. The coil 28, in addition to connecting the electrode 26 to the connector, also serves to guide the stylet 34 into engagement with the electrode 26 when the lead 20 is to be guided to its intended placement position.

Figure 2:
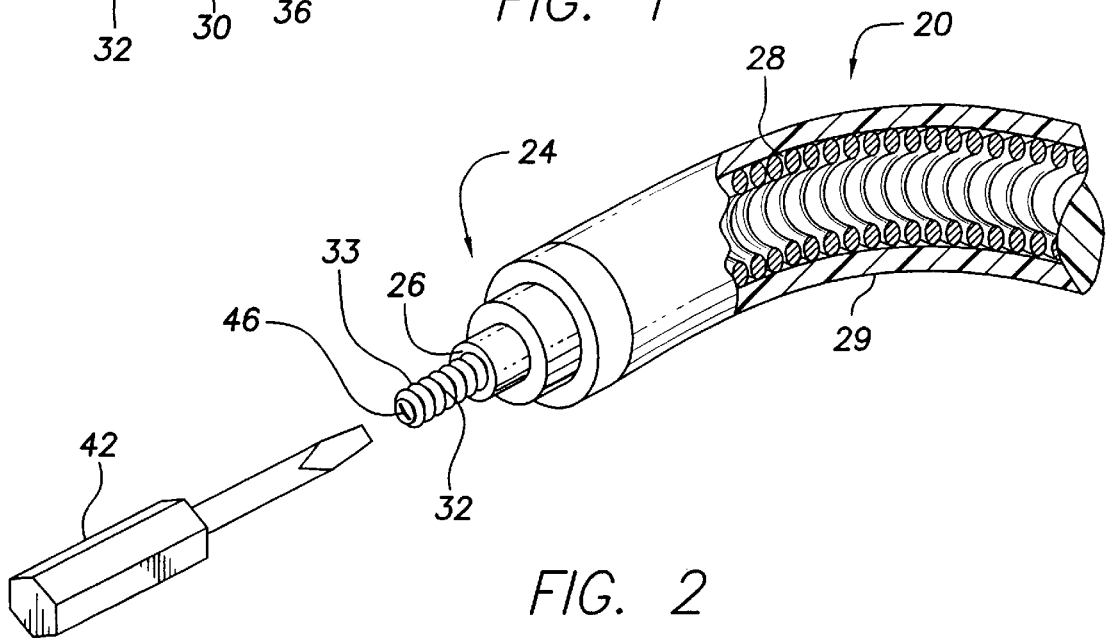
FIG. 2 is a partial perspective view and partial cross-section of the lead of FIG. 1 illustrating the adaptation of the lead from a stylet placement configuration to a guidewire placement configuration.

Referring now to FIG. 2, it illustrates the lead 20 being adapted for guidewire lead placement. The lead 20 includes a retaining mechanism for releasably retaining the plug 32 within the through bore 30. In accordance with this preferred embodiment, the retaining mechanism is formed by a thread 33 carried by the plug 32 and a complimentary thread within the through bore 30.

When the lead 20 is adapted for guidewire placement, a tool 42 having a screwdriver tip 44 engages a slot 46 formed in the distal end of the plug 32. When the tool engages the slot 46 and is turned in a counterclockwise direction, the plug 32 is rotated and removed from the through bore 30.

Figure 3:
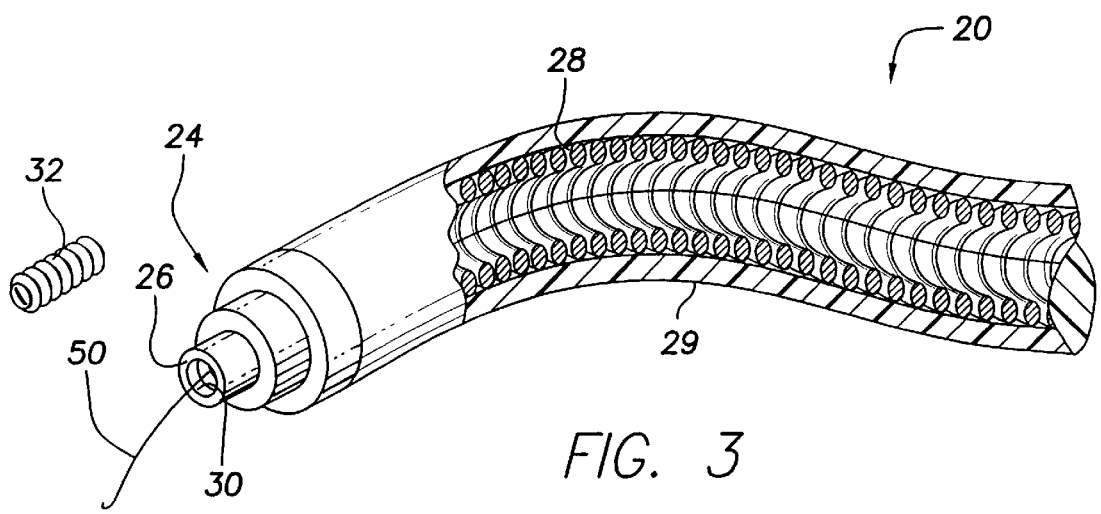
FIG. 3 shows the lead of FIG. 1 adapted for guidewire placement.

FIG. 3 illustrates the lead 20 after having been configured for guidewire lead placement. Here it will be noted that the plug 32 has been removed from the through bore 30. Also, the electrode 26 has been threaded onto the guidewire 50. In threading the guidewire 50 into the through bore 30, the stylet coil 28 serves to guide the guidewire 50 from the distal end 24 of the lead 20 to the proximal end of the lead.

As is well known in the art, when the lead 20 is to be placed in position by guidewire lead placement, the guidewire 50 is first advanced to the desired location. Thereafter, the lead 20 is advanced over the guidewire as described above using a technique commonly referred to as the "over the wire" technique. When the lead is advanced over the guidewire to the desired position, the guidewire is then withdrawn with the lead remaining in the desired position.

FIG. 4 illustrates lead 60 embodying the present invention. As shown in FIG. 4, the lead 60 is configured for stylet placement.

The lead 60 includes an elongated lead body 62 having a distal end 64 and a proximal end 65. The lead further includes an electrode 66 at its distal end 64. The electrode 66 includes a through bore 70 and a plug 72 received within the through bore. The through bore 70 and the plug 72 include complimentary threads 71 and 73 respectively for retaining the plug 72 within the through bore 70.

The lead 60 further includes a stylet coil 68 which engages a cylindrical extension 75 of the electrode 66. More specifically, the stylet coil 68 is frictionally received over the cylindrical extension 75 and extends to an electrically conductive connector 80. The stylet coil 68 electrically connects the electrode 66 with the connector 80. Overlying the stylet coil is a lead insulator 65 which, again, may be silicone rubber.

As previously mentioned, the lead 60 is configured for stylet placement. To that end, a stylet 74 is illustrated after having been advanced into the lead 60 with its distal end 76 engaging the plug 72 retained within the through bore 70 of the electrode 66.

Referring now to FIG. 5, it illustrates the lead 60 being adapted for guidewire lead placement. Here it may be seen that a tool 90 has engaged the plug 72 and is rotating the plug 72 to release the plug 72 from the through bore 70 of the electrode 66. Clearly seen in FIG. 5 are the complimentary threads 71 and 73 of the through bore 70 and plug 72 respectively.

When the plug 72 is removed as may be seen in FIG. 6, the lead 60 has been adapted for guidewire lead placement. More specifically, the lead 60 has been advanced over a guidewire 100. To that end, the lead 60 is advanced so that the through bore 70 receives the guidewire 100. As the lead is further advanced on the guidewire 100 the stylet coil 68 serves as a guide to guide the guidewire from the proximal end 64 of the lead 60 to its distal end 65. After the lead is fully on the guidewire 100, a control knob 102 is then frictionally applied to the guidewire 100 in a known manner. As previously mentioned, when the lead 60 is advances over the guidewire 100 to its desired position, the guidewire 100 is withdrawn leaving the lead in its desired position.

Figure 7:
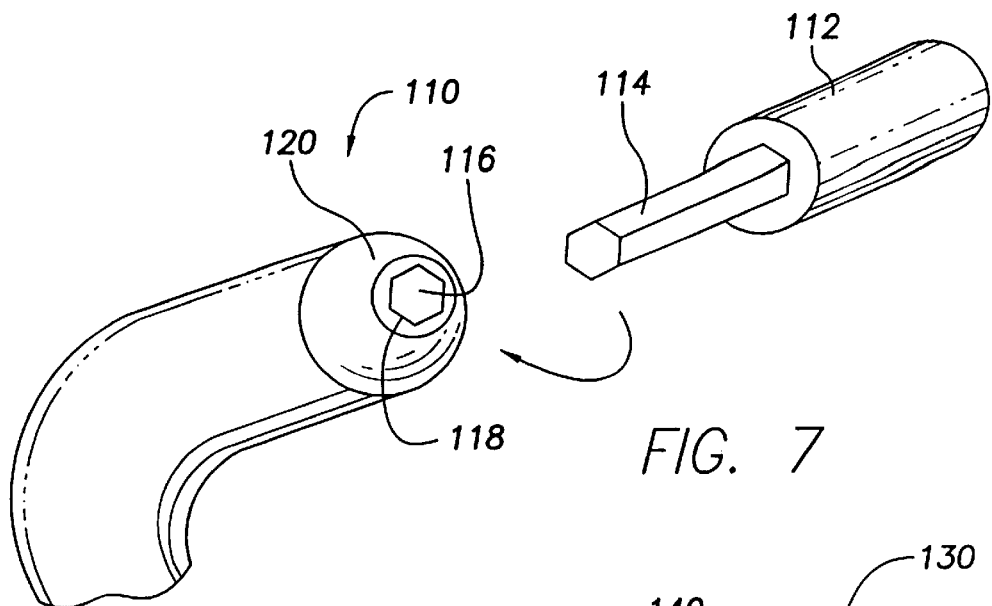
FIG. 7 is a partial perspective view of the distal end of a further implantable cardiac stimulation lead embodying the present invention shown in association with a tool for adapting the lead from a stylet placement configuration to a guidewire placement configuration.

Referring now to FIG. 7, it illustrates the distal end of another implantable cardiac stimulation lead 110 embodying the present invention. Here it may be seen that the tip 114 of a tool 112 may be inserted into a correspondingly shaped indentation 116 of a plug 108 so as to remove the plug 118 from an electrode 120 to adapt the lead 110 for guidewire lead placement. As will be seen hereinafter, the same tool 112 may be utilized for securing the connector at the distal end of lead 110 to an implantable cardiac stimulation device such as a pacemaker.

Figure 8:
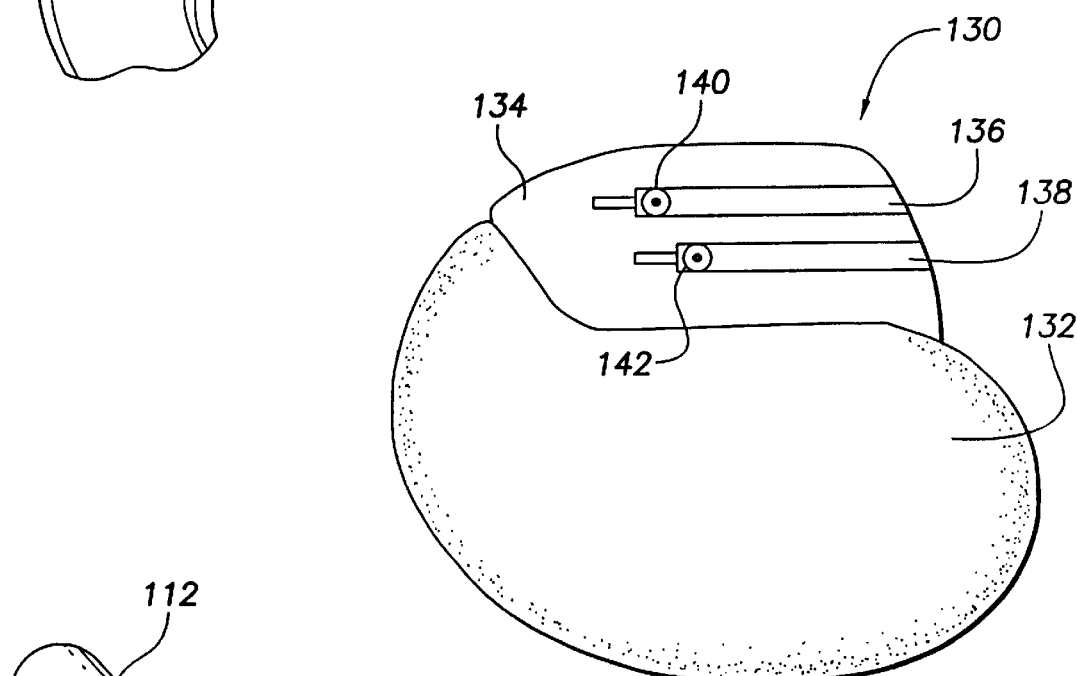
FIG. 8 is a side plan view of an implantable cardiac stimulation device of the type with which the implantable cardiac stimulation leads of the present invention may be used.

FIG. 8 illustrates such an implantable pacemaker 130. The implantable pacemaker 130 includes a case 132 and an electrically insulating header 134. Within the header 134 the pacemaker includes connector ports 136 and 138 for receiving the proximal ends of an atrial lead and a ventricular lead respectively. The ports 136 and 138 are configured to receive the connectors at the proximal ends of the atrial and ventricular leads. The connectors are retained or secured in place by set screws 140 and 142 in a manner known in the art.

Figure 9:
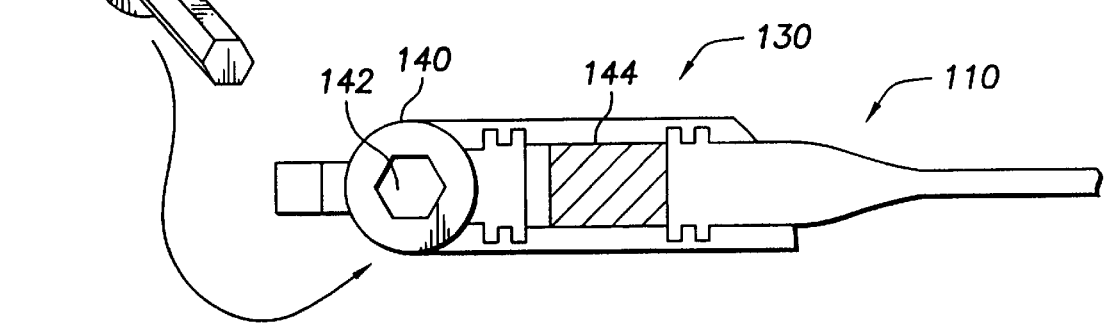
FIG. 9 is a partial top plan view of the implantable cardiac stimulation device of FIG. 8 illustrating the manner in which the connector of the implantable cardiac stimulation leads of the present invention may be secured to the implantable cardiac stimulation device using the same tool that may be used for adapting the lead placement configuration of the implantable cardiac stimulation lead of the present invention.

As can be seen in FIG. 9, the set screw 140 has an hexagonal indentation 142 which may have the same shape and dimension as the hexagonal indentation 116 of the plug 118 of FIG. 7. Hence, once the connector 144 of the lead 110 is inserted into the port 136, for example, the tool 112 may be used to rotate the set screw 140 to secure the proximal end of the lead to the pacemaker 130 and thus retain electrical connection between the lead 110 and the pacemaker 130.

Figure 10:
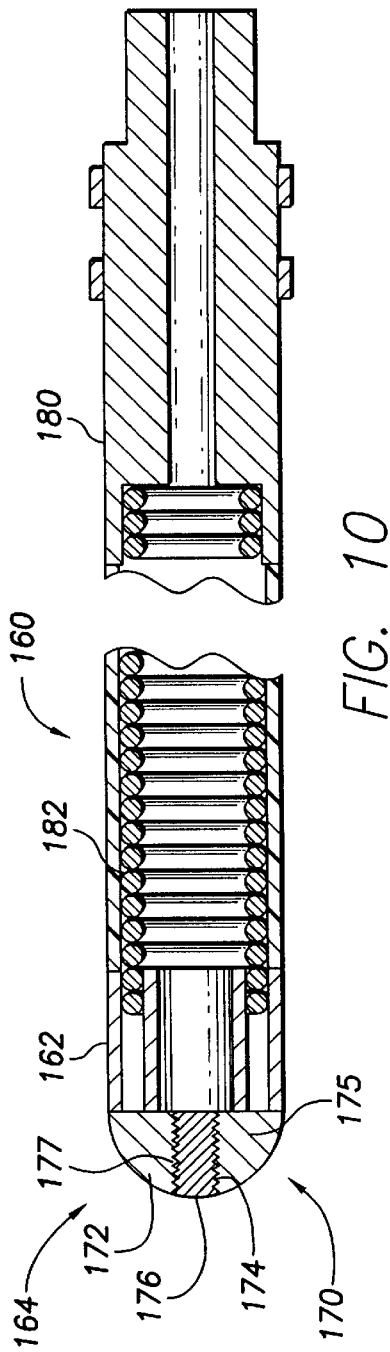
FIG. 10 is an exploded cross-sectional view illustrating a still further implantable cardiac stimulation lead embodying the present invention.

Referring now to FIG. 10, it illustrates a still further implantable cardiac stimulation lead 160 embodying the present invention. Here, the lead 160 includes a ring electrode 162. At the distal end 164 of the lead 160 is an implanting guide structure 170. The implanting guide structure adapts the lead 160 for either stylet placement or guidewire lead placement. More specifically, the implanting guide structure includes a rigid member 172. The rigid member may be formed of insulating material such as hardened silicone, polyurethane, or other material known in the art. The rigid member 172 includes a through bore 174. The implanting guide structure 170 further includes a plug 176 which is received within the through bore 174. The implanting guide structure 170, as in the previous embodiments, further includes a retaining mechanism in the form of complimentary threads 175 and 177 carried by the through bore 174 and plug 176 respectively.

The lead 160 includes a connector 180 at its proximal end. The connector 180 is electrically connected to the ring electrode 162 by a stylet coil 182.

When the lead 160 is to be adapted for guidewire lead placement, the plug 176 is removed from the through bore 174 by rotating the plug 176 relative to the rigid member 172. Once the plug 176 is removed from the bore 174, the lead 160 may be advanced over a guidewire as previously described.

Although complimentary threads on the plug and through bore have been described herein for releasably retaining the plug within the through bore, it will be appreciated by those skilled in the art that other mechanisms could be used to releasably retain the plug within the through bore. Such other mechanisms may include ball bearings, compression springs, or a simple bond without departing from the present invention.

When a lead is placed using guidewire lead placement, both the distal and proximal ends of the lead are open. This permits fluid to flow into the lead from either end. This is especially the case when the distal end of the lead is placed into the veins of the left side of the heart and the proximal end of the lead is placed inside the pacemaker connector top located in the subcutaneous pocket. The pressure in the veins of the left side of the heart can be greater than the pressure in the subcutaneous pocket. As a result, blood may flow from the distal end of the lead to the proximal end of the lead.

Figure 11:
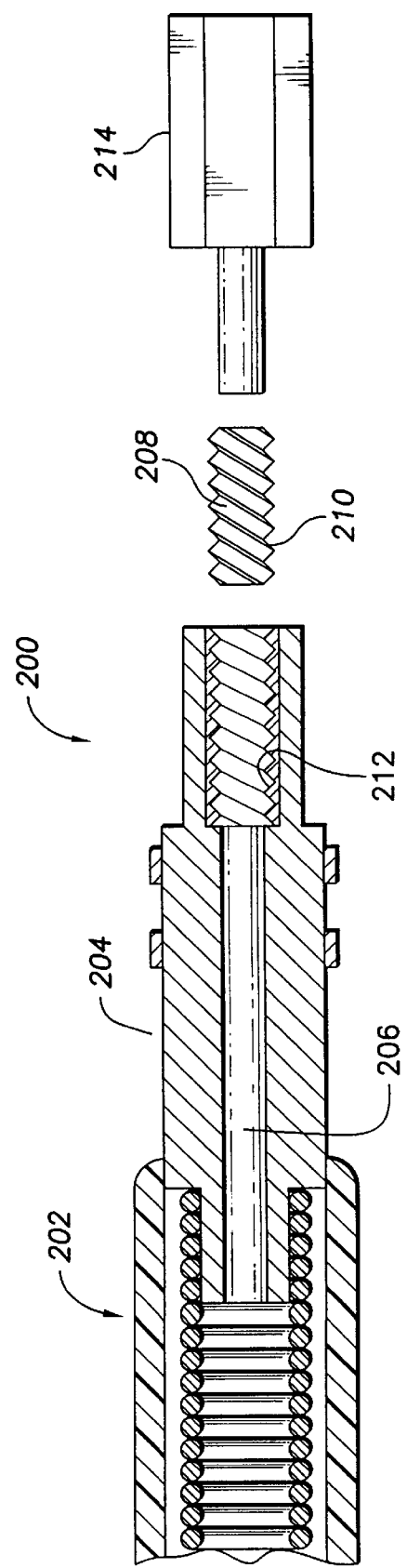
FIG. 11 is a cross-sectional side view of the connector end of an implantable cardiac stimulation lead embodying further aspects of the present invention.

FIG. 11 illustrates the proximal or connector end 200 of a lead 202 embodying the present invention which prevents blood flow into the connector top of the implantable cardiac stimulation device with which the lead 202 is utilized. The connector 204 may be used in any one of the leads previously described. As will be seen in FIG. 11, the connector 204 includes a through bore 206. A plug 208 is dimensioned to be received within the through bore 206. The plug includes an external thread 210 and the through bore 206 includes a complimentary internal thread 212. Once the lead 202 is placed in position by guidewire lead placement and after the guidewire is withdrawn from the lead, the plug 208 may be advanced into the through bore 206 by threading the plug 208 into the through bore 206 with a tool 214. With the plug 208 releasably retained within the through bore 206, blood flowing from the distal end to the proximal end of the lead will be prevented from flowing into the connector top of the implantable cardiac stimulation device.

FIG. 12 is an exploded, cross-sectional side view of an electrode 220, a plug 222 and a stylet tool 224 which permits the plug 222 to be replaced in the electrode 220 following guidewire lead placement to prevent blood flow into the lead in which the electrode 220 and plug 222 are employed. Likewise, a stylet 224 can be used to remove the plug similar to the method described above. The electrode 220 includes a through bore 226 which includes a distal portion 228 and a proximal portion 230. The proximal portion 230 is greater in diameter than the distal portion 228 and is dimensioned to receive the plug 222. The proximal portion 230 of the through bore 226 includes an internal right-handed thread 232 which is complimentary to the external right-handed thread 234 of the plug 222. The plug 222 also includes a bore 236 having an internal left-handed thread 238 which is complimentary to an external left-handed thread 240 of the stylet tool 224. The pitch of the threads 232 and 234 are different than the pitch of the threads 238 and 240 to allow the plug 222 to be advanced two times the opposite distance into the electrode as compared to the distance the stylet tool is removed out of the plug for each rotation of the stylet. This ensures that the plug 222 is locked into the electrode 220 prior to the removal of the stylet tool 224 from the plug 222.

After the lead is positioned by guidewire lead placement, the guidewire is withdrawn from the lead. The plug 222 is inserted onto the distal tip of the stylet tool 224. Next, the stylet tool 224 and the plug 222 are inserted into the proximal end of the lead and advanced to the proximal portion 230 of the through bore 226. The plug 222 is then engaged into the proximal portion 230 of the through bore 226 and the stylet tool 224 is torqued such that the stylet tool 224 is disengaged from the plug 222. The different pitch of the internal and external threads of the plug 222 allow for the plug to advance two times the opposite distance into the electrode as compared to the distance the stylet is removed out of the plug for each rotation of the stylet tool 224. This allows the stylet tool 224 to be removed from the lead while leaving the plug 222 in place within the proximal portion 230 of the through bore 226. With the plug 222 thus placed in the electrode 220, blood flow into the lead is precluded.

FIG. 13 is an exploded, cross-sectional view of another electrode 260, plug 262, and stylet tool 264 configured to provide an alternative approach for replacing the plug 262 within the electrode 260. The electrode 260 includes a through bore 266 which includes a distal portion 268 and a proximal portion 270. The proximal portion 270 of the through bore 266 includes indentations 272.

The plug 262 includes ball bearings 274 which are spring loaded by springs 276. The plug 262 is dimensioned to be received within the proximal portion 270 of the through bore 266. When the plug 262 is received within the proximal portion 270 of the through bore 266, the ball bearings 274 are received within the indentations 272 to releasably retain the plug 262 within the electrode 260.

To insert the plug 262 into the proximal portion 270 of the through bore 266, the plug 262 further includes a bore 278 having an internal thread 280. The stylet tool 264 in turn includes an external complimentary thread 282.

After the lead is positioned by guidewire lead placement, the guidewire is withdrawn from the lead. Next, the stylet tool 264 is advanced onto the plug 262 by rotating the stylet tool 264 to permit the complimentary threads 280 and 282 to engage. With the plug 262 thus being carried by the distal tip of the stylet tool 264, the stylet tool 264 and plug 262 are inserted into the proximal end of the lead and advanced to the distal tip of the lead. The plug 262 is then inserted into the proximal portion 270 of the through bore 266 of the electrode 260 until the ball bearings 274 engage the mating indentations 272 within the proximal portion 270 of the through bore 266. This will cause the plug 262 to be releasably retained within the electrode 260. Next, the stylet tool 264 is disengaged from the plug 262 and removed from the lead. With the plug 262 retained within the proximal portion 270 of the through bore 266, blood is precluded from flowing into the lead in which the electrode 260 and plug 262 are employed.

From the foregoing, it can be seen that the present invention provides an implantable cardiac stimulation lead which may be adapted for either stylet placement or guidewire lead placement. As a result, should, during surgery, it be found that guidewire lead placement would be better then stylet placement, the lead may be readily adapted for the guidewire lead placement. The adaptation of the lead is easy to perform and requires, in accordance with the preferred embodiment herein, a tool made already available to the physician for implanting the implantable cardiac stimulation device.

While the invention has been described by means of specific embodiments and applications thereof, It is understood that numerous modifications and variations could be made thereto by those skilled in the art without departing from the spirit and scope of the invention. It is therefore to be understood that within the scope of the claims, the invention may be practiced otherwise then as specifically described herein.

What is claimed is:

1. An implantable cardiac stimulation lead comprising:
   an elongated lead body having a distal end and a proximal end;
   at least one electrode carried by the lead body;
   a connector at the proximal end of the lead body;
   a conductor connecting the at least one electrode to the connector; and
   an implanting guide structure at the distal end of the lead body, the implanting structure including a rigid member including a through bore, a plug dimensioned to be received within the through bore, and a retaining mechanism that releasably retains the plug within the through bore, whereby
      when the plug is retained within the through bore, the plug is arranged for engaging a stylet for stylet placement of the lead and when the plug is released from the through bore, the through bore is arranged to receive a guidewire for guidewire placement of the lead; and
   wherein the conductor comprises a stylet coil.

2. An implantable cardiac stimulation lead comprising:
   an elongated lead body having a distal end and a proximal end;
   at least one electrode carried by the lead body;
   a connector at the proximal end of the lead body;
   a conductor connecting the at least one electrode to the connector; and
   an implanting guide structure at the distal end of the lead body, the implanting structure including a rigid member including a through bore, a plug dimensioned to be received within the through bore, and a retaining mechanism that releasably retains the plug within the through bore, whereby
   when the plug is retained within the through bore, the plug is arranged for engaging a stylet for stylet placement of the lead and when the plug is released from the through bore, the through bore is arranged to receive a guidewire for guidewire placement of the lead; and
   wherein the plug is arranged for receiving a tool for retaining the plug within the through bore, wherein the connector includes a retaining element for securing the connector to an implantable cardiac stimulation device, and wherein the retaining element is arranged for receiving the tool for securing the connector to the implantable cardiac stimulation device.

3. An implantable cardiac stimulation lead comprising:

an elongated lead body having a distal end and a proximal end;

at least one electrode carried by the lead body;

a connector at the proximal end of the lead body;

a conductor connecting the at least one electrode to the connector; and an implanting guide structure at the distal end of the lead body, the implanting structure including a rigid member including a through bore, a plug dimensioned to be received within the through bore, and a retaining mechanism that releasably retains the plug within the through bore, whereby when the plug is retained within the through bore, the plug is arranged for engaging a stylet for stylet placement of the lead and when the plug is released from the through bore, the through bore is arranged to receive a guidewire for guidewire placement of the lead; and wherein the connector includes a through bore and wherein the lead further includes a second plug dimensioned to be received within the connector through bore and a second retaining mechanism that retains the second plug within the connector through bore.

4. The lead of claim 3, wherein the second retaining mechanism includes complimentary threads on the second plug and in the connector through bore.

5. The lead of claim 4 wherein the first plug is arranged for receiving a tool for retaining the first plug within the through bore, wherein the connector includes a retaining element arranged for receiving the tool for securing the connector to an implantable cardiac stimulation device, and wherein the second plug is arranged for receiving the tool for retaining the second plug within the connector through bore.

6. An implantable cardiac stimulation lead comprising:

an elongated lead body having a distal end and a proximal end;

at least one electrode carried by the lead body;

a connector at the proximal end of the lead body;

a conductor connecting the at least one electrode to the connector; and an implanting guide structure at the distal end of the lead body, the implanting structure including a rigid member including a through bore, a plug dimensioned to be received within the through bore, and a retaining mechanism that releasably retains the plug within the through bore, whereby when the plug is retained within the through bore, the plug is arranged for engaging a stylet for stylet placement of the lead and when the plug is released from the through bore, the through bore is arranged to receive a guidewire for guidewire placement of the lead; and wherein the through bore includes a distal end and a proximal end and wherein the through bore is arranged for receiving the plug at the proximal end of the through bore.

7. An implantable cardiac stimulation lead comprising:

an elongated lead body having a distal end and a proximal end;

at least one electrode carried by the lead body;

a connector at the proximal end of the lead body;

a conductor connecting the at least one electrode to the connector; and an implanting guide structure at the distal end of the lead body, the implanting structure including a rigid member including a through bore, a plug dimensioned to be received within the through bore, and a retaining mechanism that releasably retains the plug within the through bore, whereby when the plug is retained within the through bore, the plug is arranged for engaging a stylet for stylet placement of the lead and when the plug is released from the through bore, the through bore is arranged to receive a guidewire for guidewire placement of the lead; and wherein the retaining mechanism includes at least one indentation within the through bore and at least one ball bearing carried by the plug arranged to be received within the at least one indentation.

8. An implantable cardiac stimulation lead comprising:

an elongated lead body having a distal end and a proximal end;

an electrode at the distal end of the lead body, the electrode having a through bore;

a plug configured to be received within the through bore;

a retaining mechanism that releasably retains the plug within the through bore;

a connector at the distal end of the lead body; and a conductor that connects the electrode to the connector, whereby when the plug is retained within the electrode bore the lead is configured for stylet placement and when the plug is released from the electrode bore, the lead is configured for guidewire placement; and wherein the conductor comprises a stylet coil.

9. The lead of claim 8 wherein the stylet coil extends from the connector to the electrode for guiding the stylet to engage the plug for stylet lead placement and for guiding a guidewire from the through bore to the connector for guidewire lead placement.

10. An implantable cardiac stimulation lead comprising:

an elongated lead body having a distal end and a proximal end;

an electrode at the distal end of the lead body, the electrode having a through bore;

a plug configured to be received within the through bore;

a retaining mechanism that releasably retains the plug within the through bore;

a connector at the distal end of the lead body; and a conductor that connects the electrode to the connector, whereby when the plug is retained within the electrode bore the lead is configured for stylet placement and when the plug is released from the electrode bore, the lead is configured for guidewire placement; and wherein the plug is arranged for receiving a tool for retaining the plug within the through bore, wherein the connector includes a retaining element for securing the connector to an implantable cardiac stimulation device, and wherein the retaining element is arranged for receiving the tool for securing the connector to the implantable cardiac stimulation device.

11. An implantable cardiac stimulation lead comprising:

an elongated lead body having a distal end and a proximal end;

an electrode at the distal end of the lead body, the electrode having a through bore;

a plug configured to be received within the through bore;

a retaining mechanism that releasably retains the plug within the through bore;

a connector at the distal end of the lead body; and a conductor that connects the electrode to the connector, whereby when the plug is retained within the electrode bore the lead is configured for stylet placement and when the plug is released from the electrode bore, the lead is configured for guidewire placement; and wherein the connector includes a through bore and wherein the lead further includes a second plug dimensioned to be received within the connector through bore and a second retaining mechanism that retains the second plug within the connector through bore.

12. The lead of claim 11, wherein the second retaining mechanism includes complimentary threads on the second plug and in the connector through bore.

13. The lead of claim 12, wherein the plug is arranged for receiving a tool for retaining the plug within the through bore, wherein the connector includes a retaining element arranged for receiving the tool for securing the connector to an implantable cardiac stimulation device, and wherein the second plug is arranged for receiving the tool for retaining the second plug within the connector through bore.

14. An implantable cardiac stimulation lead comprising:

an elongated lead body having a distal end and a proximal end;

an electrode at the distal end of the lead body, the electrode having a through bore;

a plug configured to be received within the through bore;

a retaining mechanism that releasably retains the plug within the through bore;

a connector at the distal end of the lead body; and a conductor that connects the electrode to the connector, whereby when the plug is retained within the electrode bore the lead is configured for stylet placement and when the plug is released from the electrode bore, the lead is configured for guidewire placement; and wherein the through bore includes a distal end and a proximal end and wherein the through bore is arranged for receiving the plug at the proximal end of the through bore.

15. An implantable cardiac stimulation lead comprising:

an elongated lead body having a distal end and a proximal end;

an electrode at the distal end of the lead body, the electrode having a through bore;

a plug configured to be received within the through bore;

a retaining mechanism that releasably retains the plug within the through bore;

a connector at the distal end of the lead body; and a conductor that connects the electrode to the connector, whereby when the plug is retained within the electrode bore the lead is configured for stylet placement and when the plug is released from the electrode bore, the lead is configured for guidewire placement; and wherein the retaining mechanism includes at least one indentation within the through bore and at least one ball bearing carried by the plug arranged to be received within the at least one indentation.

* * * * *